United States Patent [19]

Kurtz et al.

[11] 4,412,536
[45] Nov. 1, 1983

[54] ORTHOPEDIC FOOT SPLINT

[75] Inventors: Robert J. Kurtz, New York; Joseph LiCausi, Port Jefferson Station, both of N.Y.

[73] Assignee: BioResearch, Farmingdale, N.Y.

[21] Appl. No.: 343,555

[22] Filed: Jan. 28, 1982

[51] Int. Cl.³ .............................................. A61F 3/00
[52] U.S. Cl. ................................................. 128/80 A
[58] Field of Search ................ 128/80 A, 80 R, 87 R, 128/88

[56] References Cited

U.S. PATENT DOCUMENTS

| 2,482,646 | 9/1949 | Brachman et al. | 128/80 A |
| 3,487,829 | 1/1970 | Barnett | 128/80 R |
| 4,249,523 | 2/1981 | Bidwell | 128/80 A |

Primary Examiner—John D. Yasko
Attorney, Agent, or Firm—Larson and Taylor

[57] ABSTRACT

An adjustable orthopedic foot splint is disclosed which maintains a desired angle between the feet of the user and which otherwise allows virtually full freedom of movement of the feet except for an undesired movement of one foot in front of or too close to the other foot as the user walks. The orthopedic foot splint includes a linkage having two pairs of parallelogram links. These parallelogram links are pivotable in a horizontal plane relative to each other and relative to the plate which engages the shoe. Attached between opposed links of one pair of parallelogram links is a tether. The tether prevents the one pair of links from pivoting beyond a predetermined angle.

8 Claims, 2 Drawing Figures

ORTHOPEDIC FOOT SPLINT

FIELD OF THE INVENTION

This invention relates generally to the field of orthopedic splints which maintain a desired angle between the feet, and more particularly to such a device which prevents one foot or both from rotating in a specified mode.

BACKGROUND OF THE INVENTION

In general, an orthopedic foot splint is useful in correcting bone deformities, particularly in children, by holding the patient's feet at an appropriate corrective angle. Thus, if a patient's feet are abnormally toed-in, it is recommended that the patient wear a splint for a specified period which will hold the feet in a corrective toed-out position. A common type of prior art device, as disclosed in U.S. Pat. Nos. 2,920,620 to Rogers; 4,040,416 to Zentman; and 4,008,129 to DiGiulio, includes a pair of shoes mounted on a flat bar. The shoes in these devices are adjustable on the bar to provide a variety of different toe-in and toe-out angles, but are not otherwise adjustable. Unfortunately, these prior art devices are extremely uncomfortable to the patient as they maintain the feet in almost rigid positions. Even the patent to Zentman which includes a flexible spacer bar to allow a slight amount of vertical movement does little to alleviate this problem. In addition, the patient cannot move except by hopping, which is dangerous and perhaps impossible for young children to perform.

To overcome this almost total lack of mobility and extreme discomfort, prior art devices have been proposed which do allow some movement as well. For instance, in U.S. Pat. No. 2,963,020 to Moran, a device is disclosed which comprises a separate member attached to each shoe of the patient which members are connected by parallelogram links. These linkages are pivotally attached to each shoe member and this allows movement of the feet both upwards and downwards, and forwards and rearwards. In addition, the length of the linkages is manually adjustable. U.S. Pat. No. 3,487,829 to Barnett also discloses parallelogram links connecting shoe engaging members. In this device, the parallelogram links are attached to the shoe engaging members by ball and socket joints. This device also allows the feet to move forwards and backwards, and upwards and downwards, as well as allowing the ends of the shoes to tilt upwards or downwards somewhat.

In U.S. Pat. No. 4,249,523 to Bidwell, an adjustable orthopedic foot splint to which a pair of shoes are attached is disclosed which maintains a desired angle between the shoes but which otherwise allows virtually full freedom of movement of the shoes. While the foot splint disclosed in the patent is a vast improvement over the prior art types of foot splint mentioned above, some users additionally have a problem with one foot (usually the left foot) moving directly in front of the opposite foot while walking. This is especially a problem for infants as they first learn to walk.

SUMMARY OF THE INVENTION

The present invention provides a novel apparatus for holding a patients feet at a desired angle and for preventing one foot from rotation in a specified direction while the user walks, crawls or kicks.

An object of the present invention is to provide a device which maintains a patient's feet at a desired angle while still providing the feet with almost full mobility except that one foot is not allowed to rotate in a specified direction. Thus, the patient can walk, crawl or kick in an approximately normal manner and is prevented from walking, crawling or kicking in an abnormal manner.

It is a feature of the present invention to use a pair of parallelogram links to connect and maintain the patient's feet at a desired angle. In addition, it is a further feature of the present invention to provide various pivot means in the device to allow almost unlimited movement of the feet. However, a tether is provided between at least one pair of parallelogram links to prevent that pair of parallelogram links from pivoting in a horizontal plane beyond a predetermined angle with respect to the longitudinal axis of the foot of the user.

Other features, objects, and advantages of the present invention are stated in or apparent from the detailed description of the presently preferred embodiment of the invention found hereinbelow.

DETAILED DESCRIPTION OF THE PREFERRED EMBODIMENT

Figure 1:
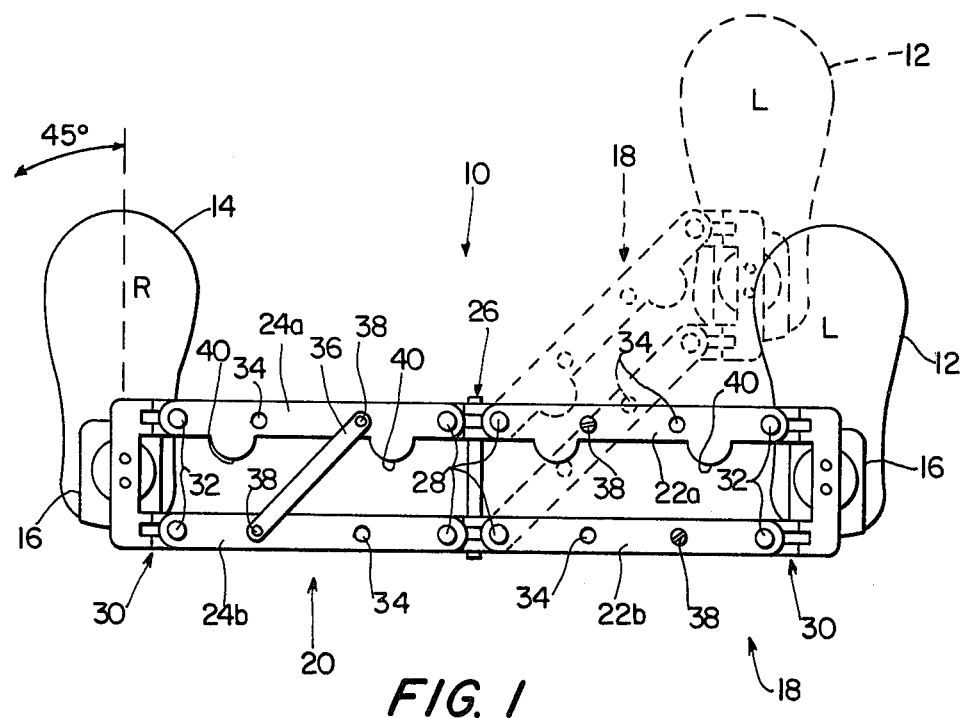
FIG. 1 is a bottom plan view of an orthopedic foot splint showing the function of the tether during movement of the left foot.
Figure 2:
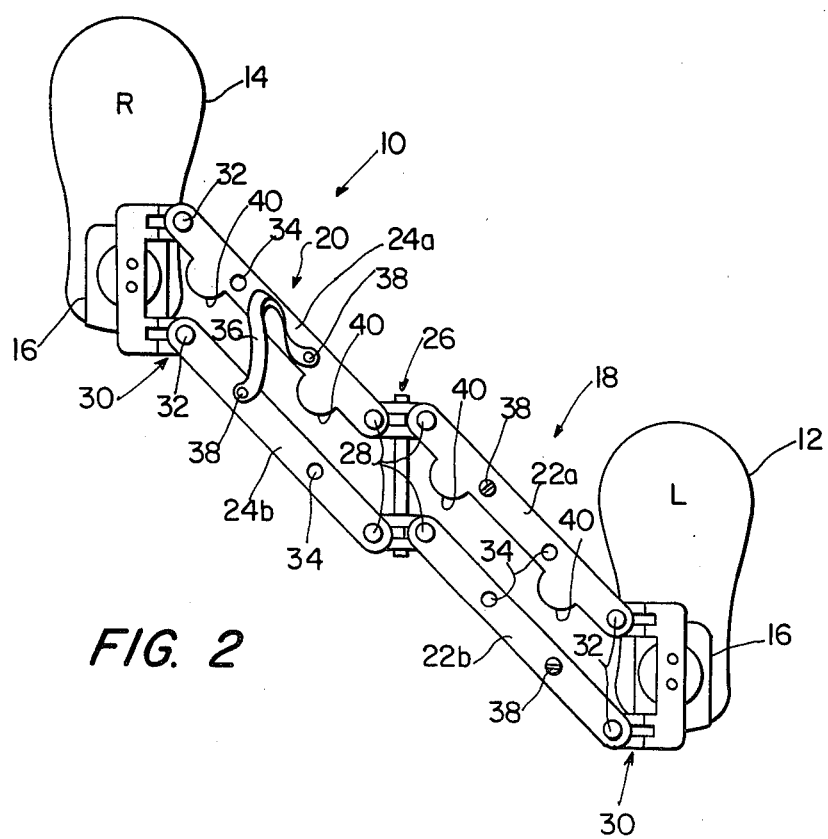
FIG. 2 is a bottom plan view of the orthopedic foot splint depicted in FIG. 1 showing the freedom allowed by the tether while the right foot moves forward during walking.

With reference now to the drawings in which like numerals represent like elements throughout the several views, a presently preferred embodiment of the present invention is depicted in FIGS. 1 and 2 and includes an orthopedic foot splint 10 of the type described in applicant's U.S. Pat. No. 4,249,523, which patent is hereby incorporated by reference. Each patient using foot splint 10 wears a special pair of fitted shoes, such as left shoe 12 and a right shoe 14. Each shoe 12 and 14 is attached to a shoe engaging plate 16. As detailed in the patent, each shoe engaging plate includes a means to adjustably attach shoe 12 or 14 to respective shoe engaging plates 16 at a plurality of different angular orientations in the horizontal plane. With this means, the toeing-in or toeing-out of the feet can be corrected as desired.

Foot splint 10 also includes two pair of parallelogram links 18 and 20. Parallelogram link 18 has two links 22a and 22b which are parallel to one another and, similarly, parallelogram link 20 has two links 24a and 24b. As shown, parallelogram links 18 and 20 are connected to each other by a central pivot 26. Central pivot 26 allows parallelogram links 18 and 20 to pivot about an axis substantially parallel with the longitudinal axis of shoes 12 and 14. Links 22a, 22b, 24a, and 24b are pivotally attached to central pivot 26 by rivets 28.

Each shoe engaging plate 16 is attached to a shoe pivot means 30. The other end of lengths 22a, 22b, 24a, and 24b are, respectively, attached by rivets 32 to the other side of shoe pivot means 30. In this manner, parallelogram lengths 18 and 20 can pivot, respectively, about a line parallel to the longitudinal axis of the respective shoe 12 or 14. In addition, links 22a, 22b, 24a, and 24b can also pivot in a horizontal plane.

Each link 22a, 22b, 24a, and 24b has a pair of threaded holes 34 therein. Preferably, as shown in FIG. 1, holes 34 in one link are opposite to holes 34 in the other link. A tether 36 is attached to links 24a and 24b by screws 38 which are received in threaded holes 34. As shown in FIG. 1, tether 38 is attached between diagonally opposed holes 34 and forms an acute angle with respect to the longitudinal axis of shoe 14. Tether 36 is flexible and preferably formed from a nylon strap.

Projecting horizontally from links 22a and 24a towards respective lengths 22b and 24b are stops 40. Stops 40 are integrally formed with respective links 22a and 22b.

In operation, orthopedic foot splint 10 functions in the following manner when attached to a user who has difficulty with one foot, usually the left foot, rotated in an inward direction. In many instances, the user will also have a problem with toe-in or toe-out and this is initially corrected by adjusting shoe engaging plate 16 as explained in the patent mentioned above. It is also possible that the user also needs corrective action on the forefoot in which case a special two piece shoe can be used as disclosed in applicant's pending U.S. Application entitled "Adjustable Orthopedic Shoe for a Foot Splint" filed on Jan. 13, 1982, Ser. No. 339,058 and herein incorporated by reference. Once the proper adjustments are made to shoes 12 and 14, tether 36 is attached by screws 40 to the appropriate holes 34. In the preferred embodiment, tether 36 is selected to be of a size so that links 24a and 24b cannot pivot beyond a line perpendicular to the longitudinal axis of shoe 14.

Shown in FIG. 2 is the position of shoes 12 and 14 of the user when left shoe 12 is about to be brought forward. In this case, it is left shoe 12 which must be restrained during walking to prevent left shoe 12 from moving in front of right shoe 14 as left shoe 12 is brought forward. Thus, as left shoe 12 is brought forward, parallelogram links 18 and 20 are free to pivot about rivets 28 and 32 and left shoe 12 is brought forward to the position shown in the solid lines in FIG. 1. It should be noted that parallelogram links 18 and 20 maintain left shoe 12 separated from right shoe 14 as left shoe 12 is brought forward. Once links 24a and 24b of parallelogram link 20 reach a position where links 24a and 24b are substantially perpendicular to the longitudinal axis of right shoe 14, tether 36 is taunt. Thus, tether 36 prevents parallelogram link 20 from pivoting forward any further. As parallelogram link 18 is free to pivot further, left shoe 12 is brought forward to the position shown by the dotted lines in FIG. 1. If left shoe 12 is brought slightly forward of the position shown in dotted lines in FIG. 1, stops 40 on link 22a prevents left shoe 12 from moving any further. Thus, the closest that left shoe 12 can get to right shoe 14 is the distance of links 24a and 24b plus whatever forward movement is allowed by stops 40 of links 22a and 22b. This position is approximately shown by the dotted outline of left shoe 12.

During the next step, as right shoe 14 is brought forward of left shoe 12, shoes 12 and 14 assume the position as shown in FIG. 2. It should be noted that as right shoe 14 is brought forward, links 24a and 24b as well as links 22a and 22b pivot so that screws 38 holding tether 36 in place move towards one another. Therefore, tether 36 must be flexible to allow this movement as shown in FIG. 2. Again, the forward movement of right shoe 14 is ultimately restrained by stops 40 on links 22a and 24a. At this point, left shoe 12 can be brought forward again as described above.

Although the present invention has been described where right shoe 14 is prevented from rotating in an inward direction, the present invention can also easily be adapted to prevent right shoe 14 from rotating in an outward direction. To accomplish this, tether 36 is replaced on parallelogram link 20 and inserted between points 34 by screws on links 24a and 24b. In addition, if the user has a problem with both shoes rotating parallel in either the outward or inward direction, two tethers 36 can be used. Where two tethers are used, the tethers should be attached at the positions indicated by screws 38 and 34 on parallelogram links 18 and 20 so that the longitudinal axis are parallel. If two tethers 36, one on links 24a and 24b and the other on links 22a and 22b, are positioned so as to intersect with one another, walking movement of shoes 12 and 14 is prevented.

It should be appreciated that foot splint 10 is designed to provide the user with almost complete freedom of movement, including bringing shoes 12 and 14 together if desired. Thus, even though during normal crawling, parallelogram links 18 and 20 with use of tether 36, prevents shoe 12 from rotating in an inward direction, it is possible for the user to purposefully move shoe 12 towards shoe 14 about central pivot 26. Because of the many movements allowed by foot splint 10 while still aligning the feet with respect to one another and preventing crossing of one shoe in front of the other, foot splint 10 is especially useful with small children first learning to walk. The young child using foot splint 10 has freedom of movement of the feet except for that being corrected.

It should also be appreciated that instead of attaching tether 36 to parallelogram link 20, tether 36 can be attached to parallelogram link 18 at the same orientation. The same movements of shoes 12 and 14 as indicated above are still allowed with this configuration. However, instead of parallelogram link 20, parallelogram link 18 is restrained from moving beyond a line perpendicular to the longitudinal axis of shoe 12. Thus, as shoe 12 moves laterally forward of shoe 14, it is parallelogram link 20 which is unrestrained and pivots forward.

Although the present invention has been described with respect to an exemplary embodiment thereof, it will be understood by those of ordinary skill in the art that variations and modifications may be affected within the scope and spirit of the invention.

What is claimed is:
1. An orthopedic foot splint comprising:
  a pair of shoe engaging plates for engaging shoes having longitudinal axis;
  linkage means for interconnecting said pair of shoe engaging plates, said linkage means including two pairs of parallelogram links which are pivotable in a horizontal plane relative to each other and to the respective shoe engaging plate; and
  a flexible nonextensible tether attached to opposed links of one of said pair of parallelogram links, said tether being positioned at an angle across said one pair of parallelogram links when said links are extending perpendicular from the shoe such that said one pair of links are prevented from pivoting in the horizontal plane beyond a predetermined angle with respect to the longitudinal axis of the adjacent shoe but which can pivot in the opposite direction freely.

2. An orthopedic foot splint as claimed in claim 1 wherein said tether prevents said one pair of parallelogram links from pivoting forward relative to one of the shoes beyond a predetermined angle such that as the other shoe moves forward relative to the first shoe, the other shoe is maintained at a predetermined lateral distance away from said first shoe.

3. An orthopedic foot splint as claimed in claim 2 wherein said one pair of parallelogram links are prevented by said tether from moving forward beyond a position where said one pair of parallelogram links are substantially perpendicular to the longitudinal axis of the shoe.

4. An orthopedic foot splint as claimed in claims 1 or 3 further including a stop located between each of said pair of parallelogram links to prevent said links from pivoting in a horizontal plane beyond a predetermined angle on either side of a line perpendicular to the longitudinal axis of the adjacent shoe.

5. An orthopedic foot splint as claimed in claim 4 wherein said stops are integrally formed in each of said pair of parallelogram links.

6. An orthopedic foot splint as claimed in claims 1 or 3 wherein said tether is a flexible strap.

7. An orthopedic foot splint as claimed in claim 6 wherein said strap is made of nylon and is attached to said pair of parallelogram links by screws.

8. An orthopedic foot splint as claimed in claims 1 or 3 wherein a tether is provided on each said pair of parallelogram links.

* * * * *